(12) United States Patent
Vahidi et al.

(10) Patent No.: US 11,684,926 B2
(45) Date of Patent: Jun. 27, 2023

(54) SYSTEM AND PROCESSES FOR ISOLATION AND ENRICHMENT BY MAGNETIC SEPARATION

(71) Applicant: Zhuhai Sanmed Biotech LTD, Zhuhai (CN)

(72) Inventors: Behrad Vahidi, Thousand Oaks, CA (US); William M. Strauss, Westlake Village, CA (US); Mike Trejo, Thousand Oaks, CA (US); Xin Ye, Zhuhai (CN); Dongwen Li, Zhuhai (CN)

(73) Assignee: ZHUHAI SANMED BIOTECH LTD., Zhuhai (CN)

( * ) Notice: Subject to any disclaimer, the term of this patent is extended or adjusted under 35 U.S.C. 154(b) by 518 days.

(21) Appl. No.: 16/510,948

(22) Filed: Jul. 14, 2019

(65) Prior Publication Data

US 2021/0008565 A1    Jan. 14, 2021

(51) Int. Cl.
| | |
|---|---|
| *B01L 9/00* | (2006.01) |
| *B03C 1/01* | (2006.01) |
| *B03C 1/28* | (2006.01) |
| *G01N 1/40* | (2006.01) |
| *G01N 35/10* | (2006.01) |
| *G01N 33/543* | (2006.01) |

(52) U.S. Cl.
CPC ............... *B01L 9/54* (2013.01); *B03C 1/01* (2013.01); *B03C 1/288* (2013.01); *G01N 1/4077* (2013.01); *G01N 33/54333* (2013.01); *G01N 35/10* (2013.01); *B01L 2300/0609* (2013.01); *B01L 2400/043* (2013.01); *B03C 2201/18* (2013.01)

(58) Field of Classification Search
None
See application file for complete search history.

(56) References Cited

U.S. PATENT DOCUMENTS

| | | | | |
|---|---|---|---|---|
| 5,705,062 A | * | 1/1998 | Knobel | B03C 1/01 210/205 |
| 6,509,193 B1 | * | 1/2003 | Tajima | B03C 1/288 436/49 |
| 2005/0118589 A1 | * | 6/2005 | Vann | C12Q 1/6816 435/6.12 |
| 2010/0047132 A1 | * | 2/2010 | Tajima | B01L 3/5085 422/400 |

\* cited by examiner

*Primary Examiner* — Matthew D Krcha
*Assistant Examiner* — Brittany I Fisher
(74) *Attorney, Agent, or Firm* — Bayramoglu Law Offices LLC (57) ABSTRACT

Systems and methods for handling a variety of sample and preparatory fluids in a rack specifically configured for compatibility with predetermined liquid handlers such as automated pipettors or multi-channel manual pipettors and set up for magnetic based sample preparation. The rack can hold all of the necessary sample and reagent vials, and present them to the pipettor in some embodiments in a way that allows for parallel operation. The rack includes slidable magnets that in some embodiments are actuatable directly by the pipettor, eliminating a layer of complexity. Combined with a suitable pipettor the magnet enabled rack supports a multistep magnetic based sample preparation capability in a high throughput manner at one station that enhances sample purity throughout magnetic separation processes.

17 Claims, 14 Drawing Sheets

SYSTEM AND PROCESSES FOR ISOLATION AND ENRICHMENT BY MAGNETIC SEPARATION

BACKGROUND

This disclosure relates to biomedical analyses using functionalized microparticles to separate or isolate target moieties from the rest of the sample. These techniques are applicable in myriad of life-sciences applications including diagnostics, therapeutics, and fundamental cell biology.

Conventional methods are prone to human error and could be cumbersome and time consuming due to the multiple operational steps involved and the need to maintain non-contamination throughout the various sample handling operations. Traditional procedures also rely on usage of multiple pieces of equipment, such as centrifuges, magnets, and macroscale filters. Increased automation and integration are desirable to improve throughput and quality for these types of analyses.

SUMMARY

Systems and methods may be provided for handling a variety of sample and preparatory fluids in a rack specifically configured for compatibility with predetermined liquid handlers such as automated pipettors or multi-channel manual pipettors and set up for magnetic based sample preparation. The rack can hold all of the necessary sample and reagent vials, and present them to the pipettor in some embodiments in a way that allows for parallel operation. The rack includes slidable magnets that in some embodiments are actuatable directly by the pipettor, eliminating a layer of complexity and manual sample handling. Combined with a suitable pipettor the magnet enabled rack supports a multi-step magnetic based sample preparation capability in a high throughput manner at a single station that enhances sample purity throughout the magnetic separation processes.

In a first aspect, an automated magnetic bead based sample preparation system is provided, including a rack, the rack including a mounting surface for vials and pipettes wherein the rack is configured to hold empty pipettes and a combination of sample and supply vials at a plurality of defined positions compatible with at least one automated pipettor, at least one slidable magnet disposed for contact or near contact with a side wall of a vial, the magnet comprising at least one of a motor actuator or nests mate-able with the pipettor heads wherein the pipettor actuates the magnets, configured to be slid adjacent to and away from at least one vial; and at least one automated pipettor compatible with the vial position spacing on the rack, the pipettor including a vertical and horizontal actuator configured to translate at least one pipettor head to the rack positions wherein the pipettor head is positioned to at least one of pick up pipettes, drop pipettes, fill vials with fluid from pipettes, and withdraw fluid from vials into pipettes at the vial positions on the rack, and pipette fill and empty fluidics in fluid communication with the pipettor head; wherein, with the rack loaded with a plurality of pipettes, empty vials and vials with fluids the system is configured to execute a magnetic based sample preparation solely in the rack to pick up pipettes, withdraw fluids from vials and place fluids in vials wherein at least one sample preparation vial is filled with a fluid sample of containing a population of magnetic beads functionally adhered to non-target moieties of biological cells, and the magnet is slid adjacent to and away from the sample preparation vial.

In one embodiment of the first aspect, the system may further include a pipette disposal position(s) accessible by the pipettor head for changing out of pipettes between fill, empty, washing, mixing, and magnet movement operations. In another embodiment of the first aspect, the supply vial positions may include sample of interest vials, washing solution vials, reagent vials, and magnetic bead suspension vials. In one embodiment of the first aspect, the rack positions may be arranged wherein multiple positions are in parallel with spacing compatible with a corresponding number of parallel pipettor heads configured to allow parallel operation on multiple vials and pipettes.

In another embodiment of the first aspect, the system may further include at least one additional slidable, magnet or set of magnets is disposed to at least one of be positionable to another side of the parallel sample preparation vials or positionable to a second set of parallel vials. In one embodiment of the first aspect, the magnets may be contoured to match the shape of at least one type of vial. In another embodiment of the first aspect, the magnets may be slidable on rails.

In one embodiment of the first aspect, the vial positions may be linearly arranged in parallel rows with the spacing between the rows set by the separation of the parallel pipettor heads. In another embodiment of the first aspect, the rack may be locked in place under the pipettor to a support surface to maintain positional accuracy for subsequent operation(s). In one embodiment of the first aspect, the magnets may be configured for negative selection sample preparation and the rack is compatible with an additional positive selection device 200 which when mated to the rack is accessible by the pipettor.

In a second aspect magnetic process for preparing magnetically separated samples may be provided including the steps of: placing empty pipettes, supply vials and sample vials in positions in a rack wherein the pipettes and vials are accessible by at least one positionable pipettor head of a pipettor, performing a series of pipette pick up, pipette drop off, washing, mixing, and vial fill/empty operations comprising; magnetically functionalizing non-target moieties of cells of a non-target in a sample preparation vial, and, positioning at least one magnet integrated with the rack adjacent at least a portion of the sample preparation vial.

In one embodiment of the second aspect, the magnetic sample process may be a negative selection process, further including drawing and holding the non-target functionalized cells to a wall of the vial; pipetting away excess fluid with increased target cell concentration from the sample vial; and optionally repeating the above steps. In another embodiment of the second aspect, each vial position and pipette position may include multiple positions in parallel accessible by multiple parallel pipettor heads and the positionable magnet or magnets are configured to access the parallel positions simultaneously.

In one embodiment of the second aspect, the supply vial positions may include sample of interest vials, washing solution vials, buffer solution vials, reagent vials and magnetic bead suspension vials. In another embodiment of the second aspect, the process may further include producing the functionalized sample solution by mixing the sample with a magnetic bead solution and optionally buffer solutions on the rack using the pipettor.

In one embodiment of the second aspect, the process may further include optionally disposing of pipette heads at a pipette disposal position(s) in between operations. In another embodiment of the second aspect, a positive selection device 200 may be mated to the rack. In one embodiment of the second aspect, the target cells may be cancer cells.

BRIEF DESCRIPTION OF THE DRAWINGS

Aspects and advantages of the embodiments provided herein are described with reference to the following detailed description in conjunction with the accompanying drawings. Throughout the drawings, reference numbers may be reused to indicate correspondence between referenced elements. The drawings are provided to illustrate example embodiments described herein and are not intended to limit the scope of the disclosure.

DETAILED DESCRIPTION OF ILLUSTRATIVE EMBODIMENTS

The current disclosure is directed to various elements of sample preparation for purification and/or separation applications and in particular to magnetic-based sample preparation. The elements include a rack implementation for holding a variety of vials for samples and sample prep reagents as well as a supply of pipettes for performing sample preparation steps. The rack has integrated magnets that are movable to be employed as necessary for magnetic cell separation operations Analytes such as cells or cellular components, can be tagged in some fashion, such as bonding to magnetic particles. When exposed to a separation mechanism, such as a magnetic field, tagged analytes can be separated from non-tagged analytes, which can result in producing samples that are high in concentration of targeted analytes.

In some embodiments magnetic separation and all other sample prep steps may be performed on the same rack. Advantageously these features allow for much faster sample prep times and less sample handling.

In some embodiments the rack may be designed to be compatible with existing pipettors. Advantageously this arrangement makes sample prep system set-up convenient and fast.

Figure 1A:
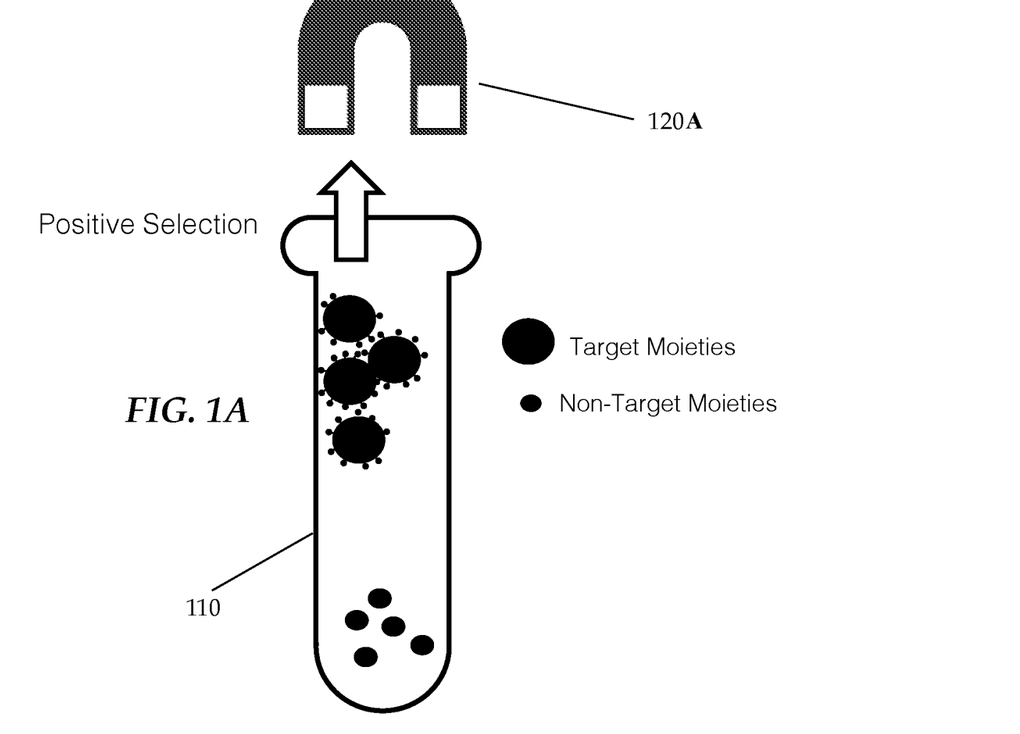
FIGS. 1A and 1B depict the difference between a positive selection sample preparation protocol and a depletion based approach.
Figure 1B:
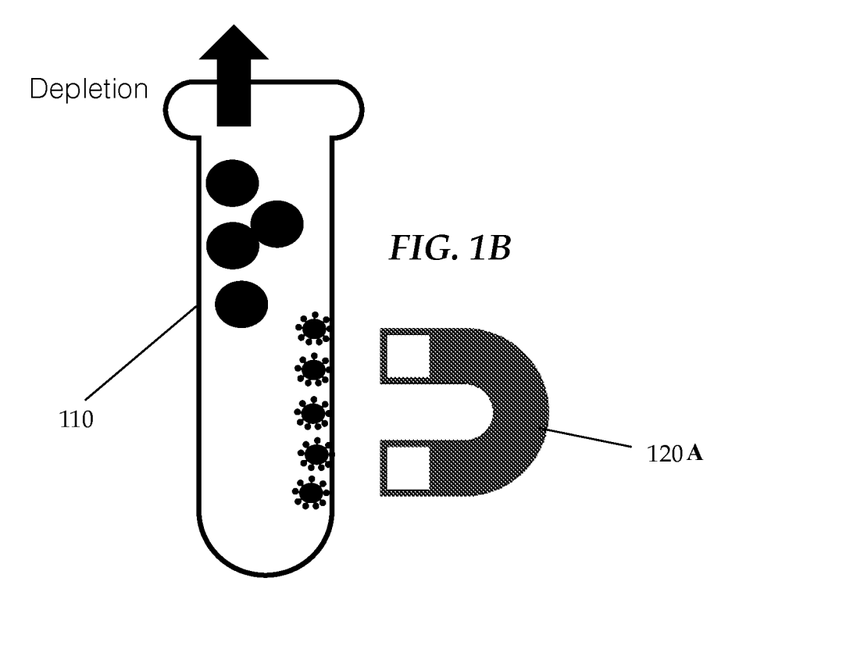

Separation approaches can be categorized into either positive or negative selection. The Positive Selection technique is illustrated in FIG. 1A. Moieties of target cells, or traces of cellular components, may bond to suitably prepared magnetic beads introduced into the sample. When a vial 110 of sample is so treated and exposed to a magnet 120A, the target moieties may be separated and drawn while the non-targeted moieties remain. An alternative but similar concept is enrichment by way of Negative Selection or Depletion, as shown in FIG. 1B. In contrast to positive selection where sample prep isolates the signal or target cells, with depletion the noise or non-target populations of cells or cellular components are eliminated. As shown, the non-targeted moieties are magnetically bonded, also referred to as magnetically functionalized. In this case the non-targeted moieties are pinned to the vial 110 wall by magnet 120A which results in a greatly enriched targeted-moieties for fluid removed from the vial, which can be then used as direct input to a number of downstream characterization methods.

Enrichment technologies by way of Depletion are of interest, mainly because they avoid some drawbacks of positive selection. Depletion may allow recovery of populations of informative cells or cellular components, which may not be captured through positive selection methods. In positive selection there maybe targeted moieties with insufficient expression of surface target markers for magnetic functionalization which may be missed by the positive selection procedures. Depletion allows for detection of moieties or targets not displaying the classical phenotype(s). Negative selection allows for more unbiased characterization of targeted moieties i.e. the targeted analytes remain unlabeled and not subject to interference with magnetic particles.

Systems and Methods described herein, combine specificity of monoclonal antibodies with the simplicity of column-free magnetic systems, i.e. the magnets can be applied laterally, which helps enable an automated tool for fast, easy, and column free elimination of non-targeted moieties with minimal sample handling.

Whether performing positive or negative selection, such sample preparation can be time and labor intensive. The current disclosure teaches techniques and system components that improve the practice.

Figure 2A:
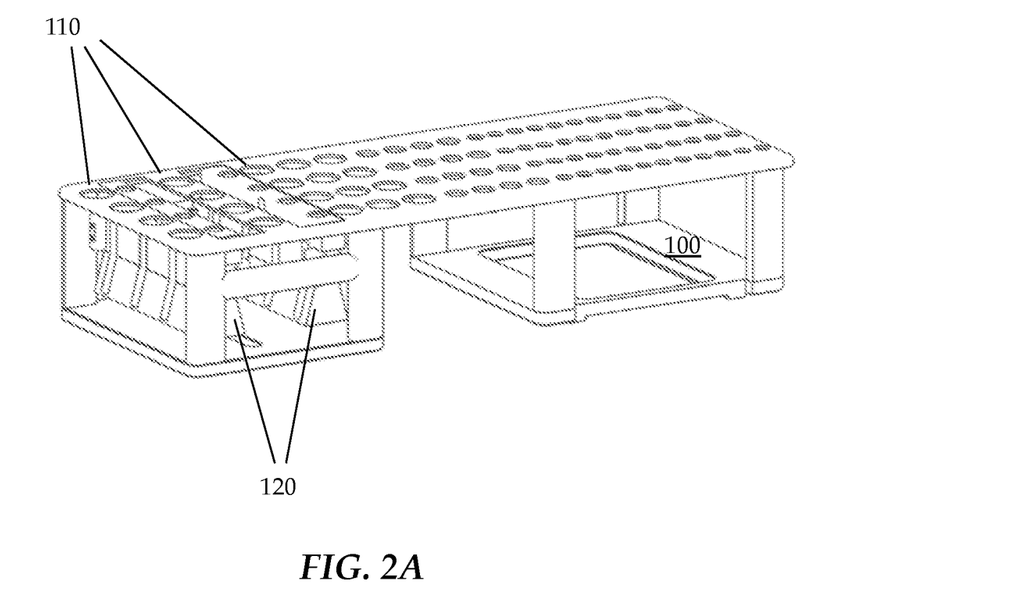
FIGS. 2A and 2B show exemplary embodiments of a rack design for automated sample preparation for both automated and manual liquid handling scenarios.
Figure 2B:
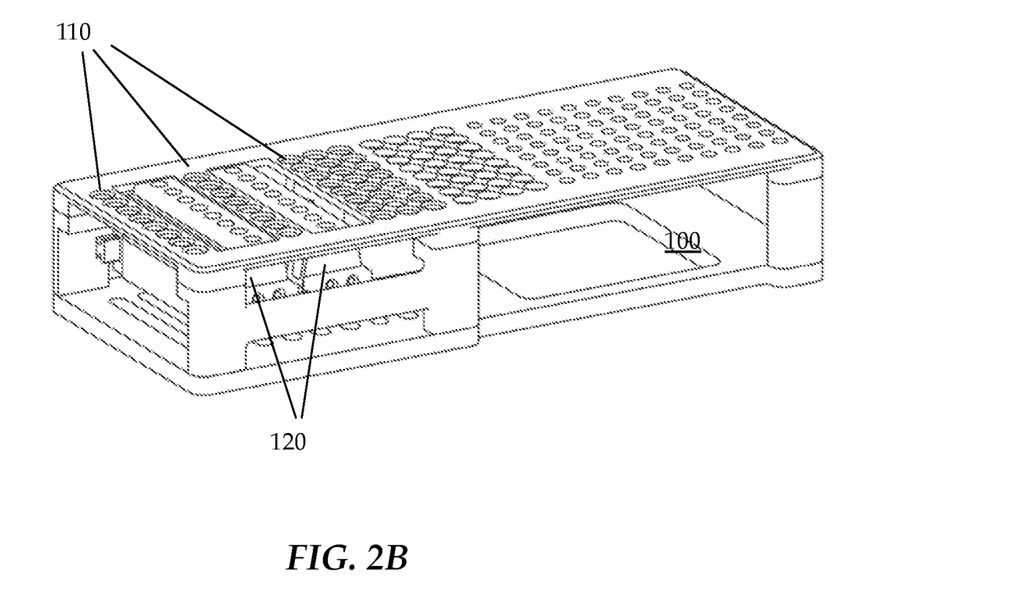

The main element for improved sample preparation is a rack system that allows for various sample preparation operations all to take place at a single station. Rack versions compatible with both automated and manual operation are disclosed. An automated system may include a multi-function rack, 100 in FIG. 2A that supports positive selection assays in addition to depletion mode protocols, herein introduced. The new rack accommodates a variety of reagent vials and disposables (such as disposable pipette tips). The rack may reside on an instrument deck. As can be seen, the rack 100 is configured with nests/mounting positions for different sized vials 110 in FIG. 3A and pipettes. In the figures, these mounting positions are shown as linear rows. Functionally there is no reason for linear rows, radial/rotating arrangements could work equally as well. For pipettors with multiple heads fixed in parallel, multiple linear rows may be useful. The Figures show an embodiment with four parallel pipette heads, so the rack has four sets of linear rows. The rack should have spacing (center-to-center dimensions) compatible with the pipettor chosen. As will be explained in more detail later, rack 100 in FIG. 2A also includes actuatable magnets 120, which are positionable to be brought adjacent to vial positions for magnetic separation processes FIG. 2B shows an integrated magnet rack more suitable for use with a manual pipettor. In this example, anywhere from 1 to a plurality of rows of vials positions 110 are adjacent to one or two rows of magnets 120, and the vials can be changed out manually as needed during the processes employed.

Figure 3A:
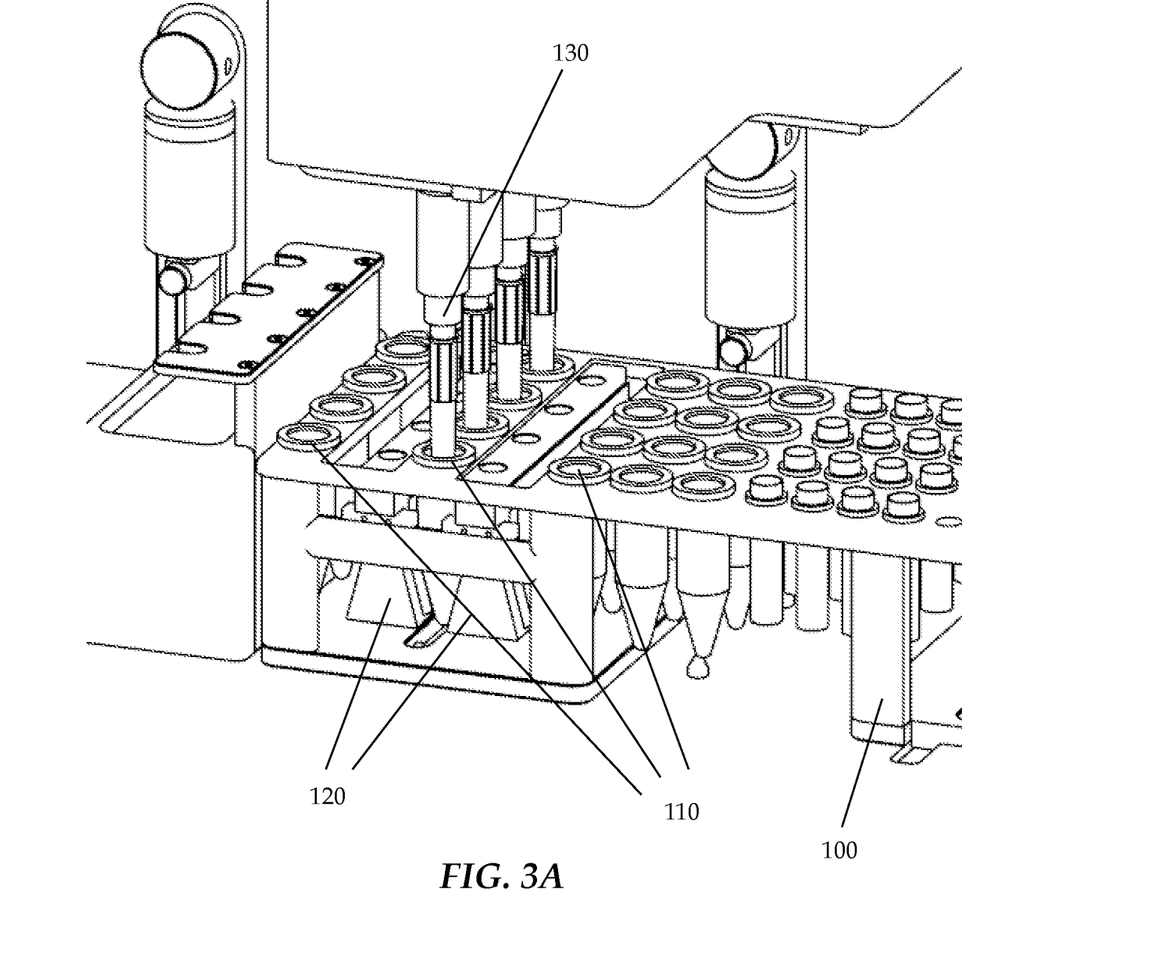
FIGS. 3A and 3B show exemplary embodiments of a system design for magnetic-based sample preparation for both automated and manual liquid handling scenarios.
Figure 3B:
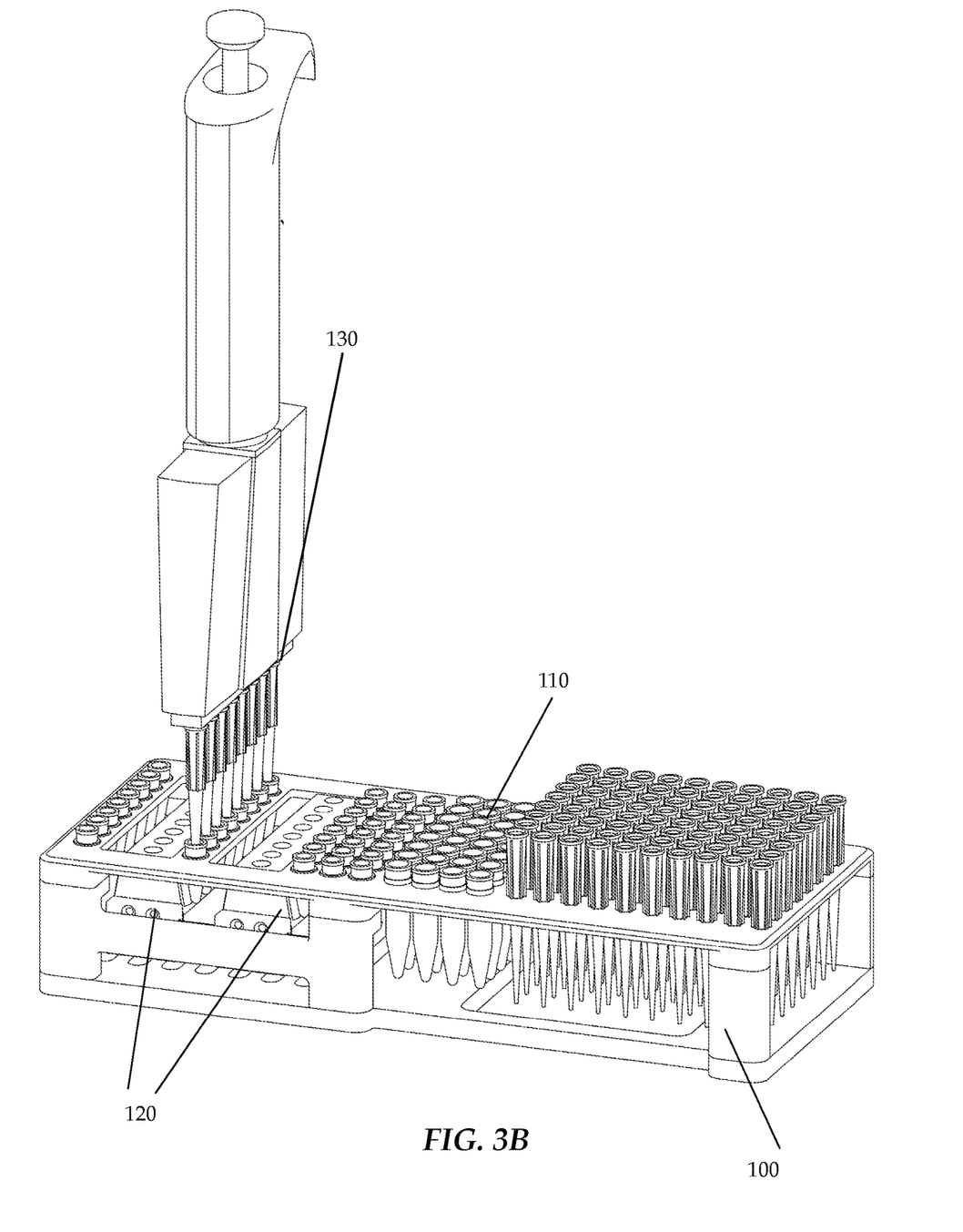

FIG. 3A shows an entire system for automated sample preparation based on the rack 100 with integrated magnets 120 and multiple vial positions 110 adjacent to one or two rows of magnets 120. In this example automated pipettor 130 is disposed above the rack and four parallel pipette heads are translatable across the linear arrangement of four parallel rows of vial positions 110 configured to be compatible with the pipettor head spacing. FIG. 3B shows all the elements of a manual system, with a linear row of manual pipettor 130 heads and a corresponding row of actuatable magnets 120. Multiple rows of vial 110 positions are possible for magnet placement/magnetic manipulation. The pipettor 130 could also pick up the various solutions required from other sources presented on the rack, to perform the mixing and separation in parallel fashion.

Figure 4A:
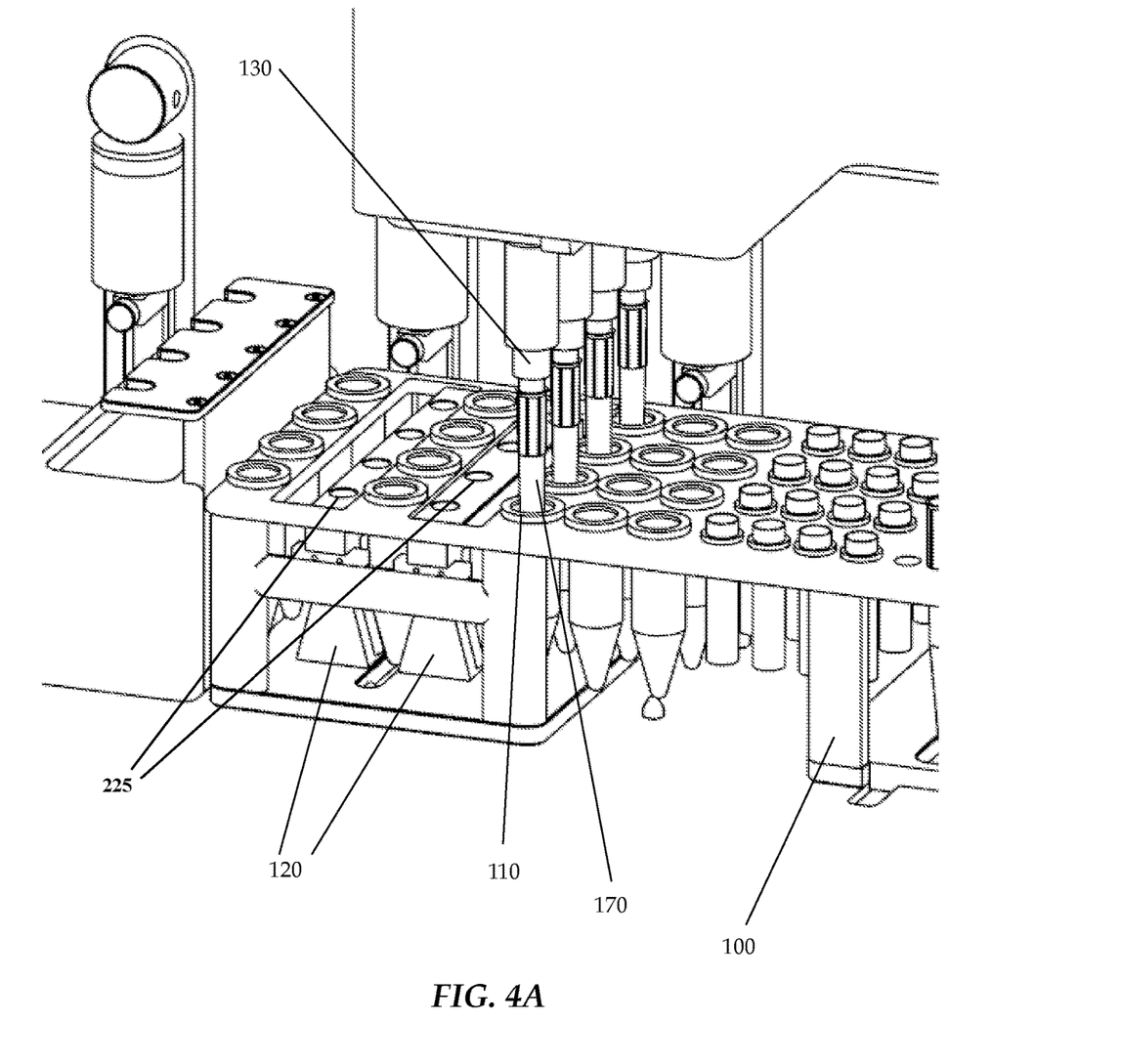
FIGS. 4A, 4B, 4C, 4D, 4E, 4F, 4G, and 4H show details of exemplary embodiments of systems for magnetic-based sample preparation for automated liquid handling scenarios.

Referring to FIG. 4A operational features are shown for the automated version. In FIG. 4A, pipettor head 130 has picked up four disposable pipettes from the right-hand side of rack 100, and has moved to a set of vials 110 for fill or drain operation.

Figure 4B:
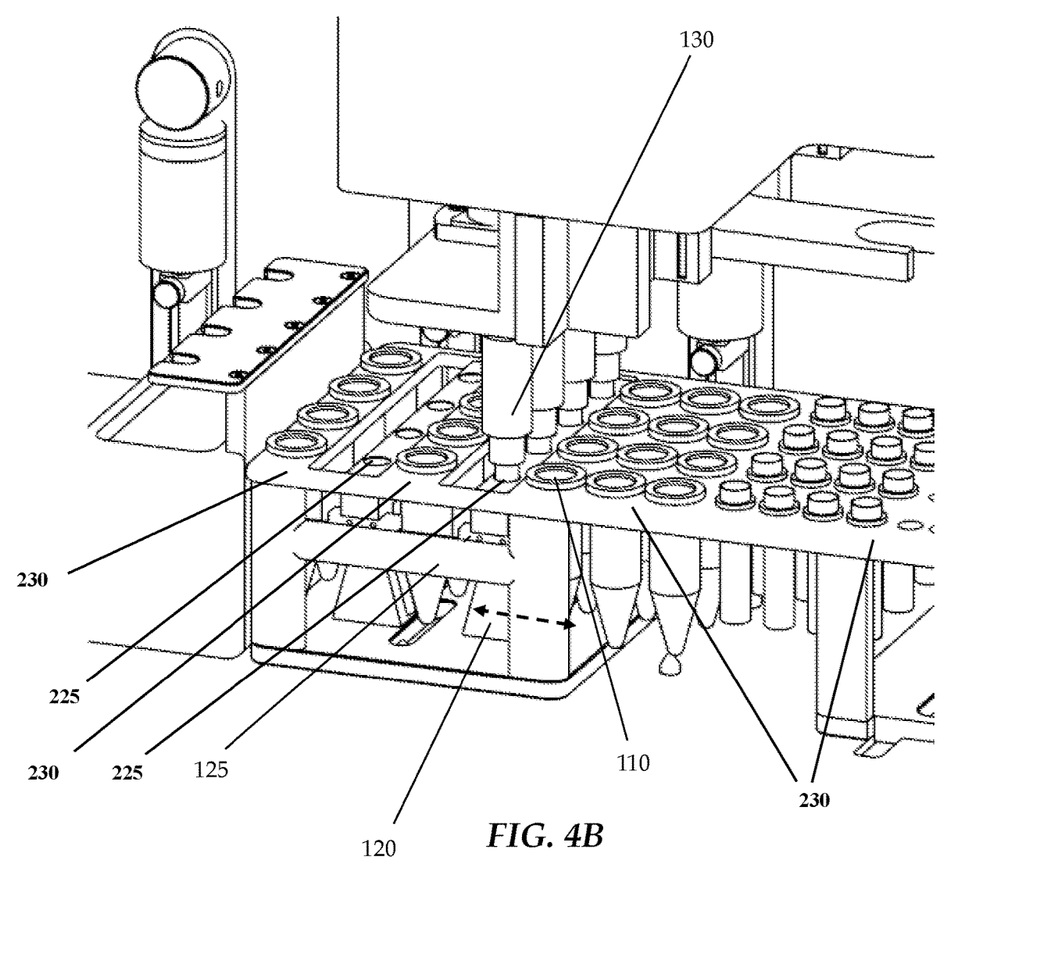
Figure 4C:
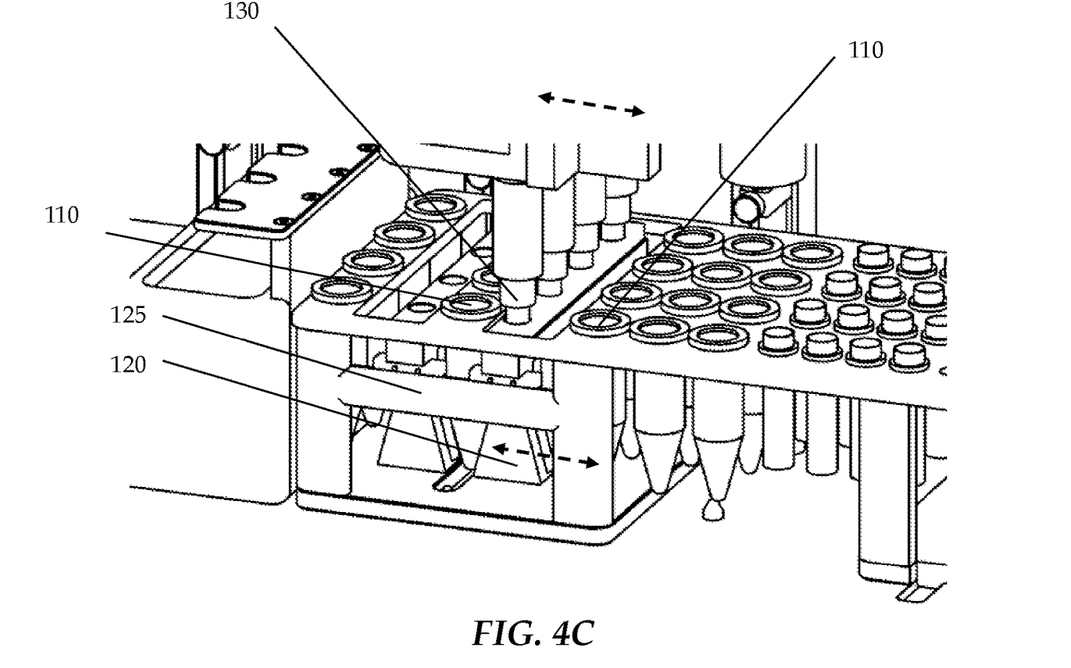
Figure 4D:
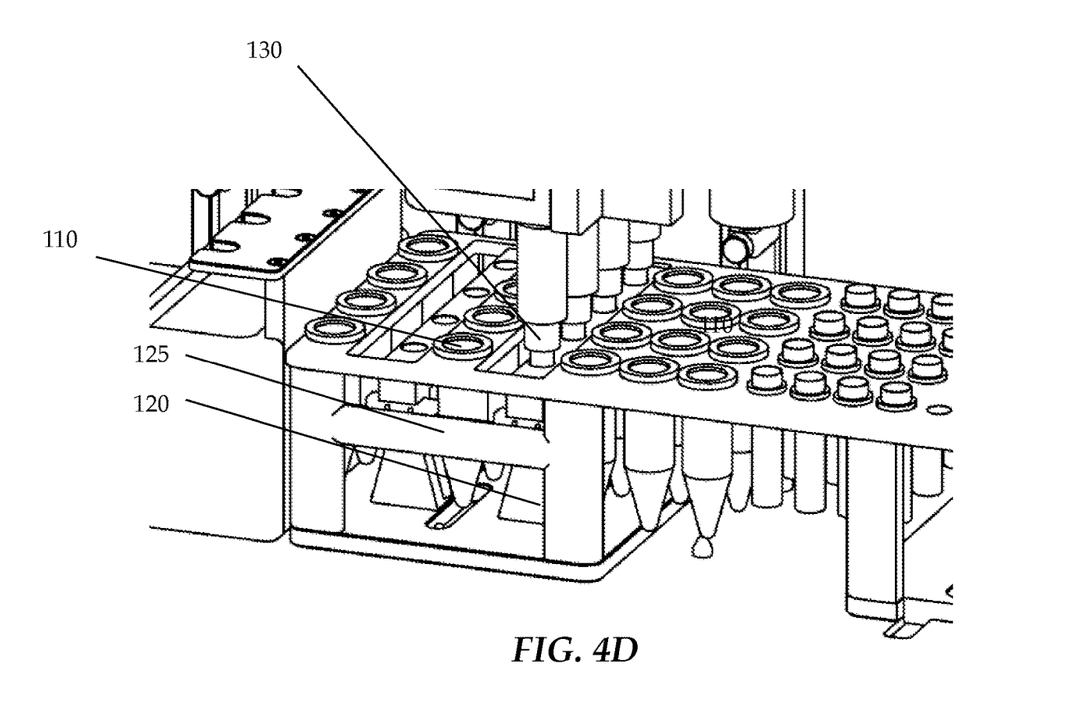
Figure 4E:
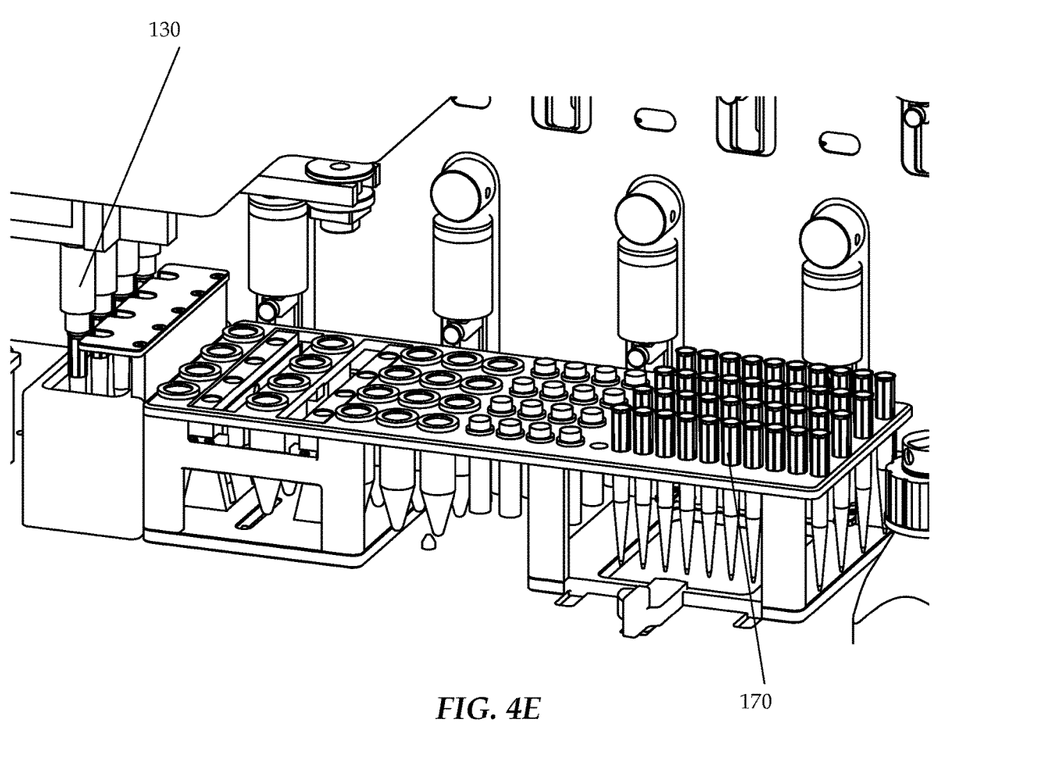

A key feature is that the rack is equipped with integrated magnets 120A, that in some embodiments operate in conjunction with the pipettor heads 130. Referring to FIG. 4B the rack is shown with a magnetic slider module, magnet/backplate arrangement 120 and rails 125, that can operate automatically during purification runs. The design could make use of a variety of magnet shapes/geometries mounted on a custom back plate to match the contours of the receptacles/tubes containing sample analyte. This results in better isolation. In FIG. 4B, the magnets are positioned adjacent to one row of vials 110 held by mounting surface 230 for separation. A variety of magnet/vial positioning could be employed. For instance, magnets may be positioned only on one row for separation, or at all rows, including from one or both sides of the vials depending on the magnet arrangement. The magnet/backplate arrangement 120 moves on linear rails 125 and can be operated by the pipettor/liquid handler. As shown in FIG. 4B Pipettor heads 130 drop down and insert in nests/holes 225 on the back plate(s) and moves the magnets on the X-axis dashed arrows, which are shown engaged with vial position 110 and in the process of moving in FIG. 4C where the magnets are engaged vial 110 and 4D with the magnets moved to disengage from middle vial position 110. Engages and disengages of the magnet are shown with the sample analyte vials through left and right linear motion operated by the pipette machine. The magnetic module locks in place once positioned by the pipettor. It can engage with various disposables on the rack from one side 4D and or from both sides 4C, providing better magnetic force fractionation. Utilizing the pipettors for both liquid handling together with engaging/disengaging of the magnets (ON/OFF) can eliminate the need for added devices, such as mechanical grippers that would pick up the tubes and deliver them to stationary magnetic nests on deck of the instrument. FIG. 4E demonstrates the pipette head ejecting pipette tips, either for picking up new set of tips for mixing, liquid transfer, or for engaging/disengaging the magnets. This feature allows more effective use of real estate on instruments decks and/or bench top space. In another embodiment of the invention the magnetic module can be operated by a motor if such an implementation is more suitable for some pipettor designs.

Figure 4F:
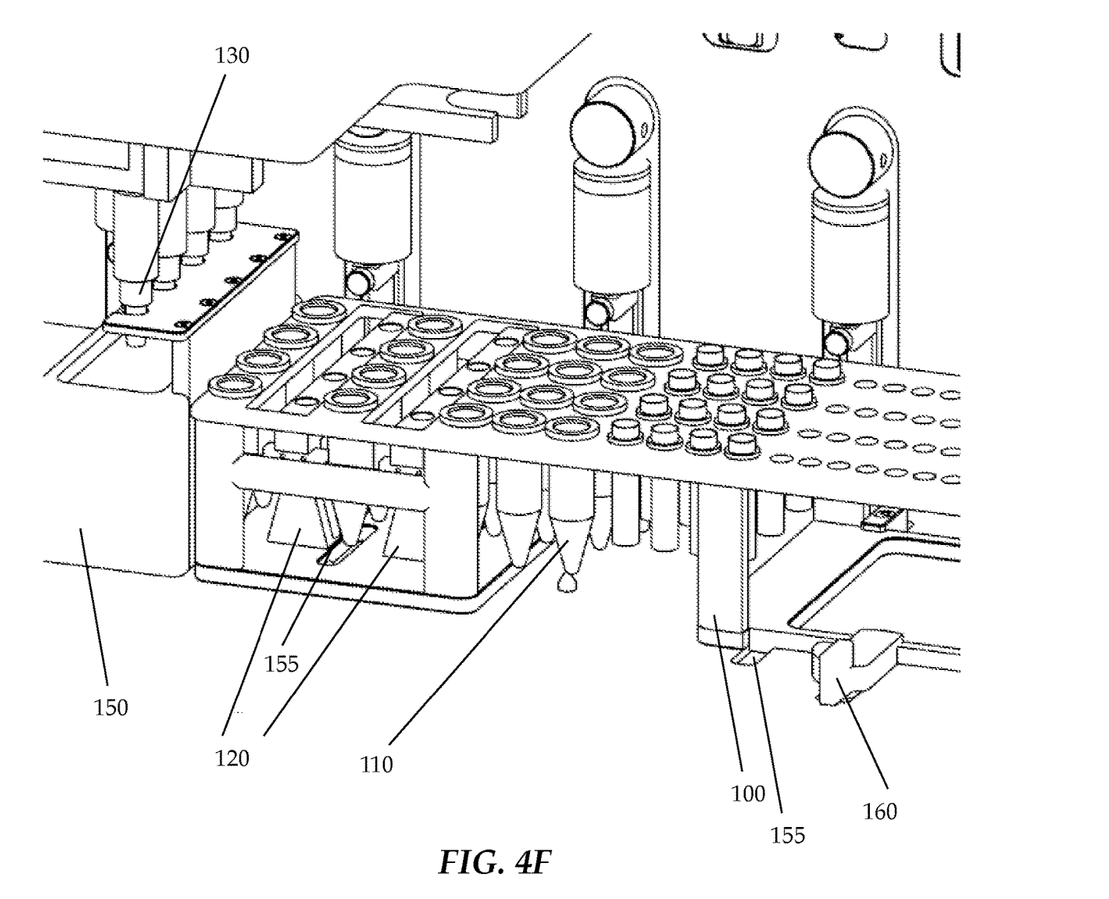

Other features are shown in FIG. 4F, using the automated system by way of an example. These features may be applicable to the manual system as well. In order to maintain sample purity, pipettes should be changed out between most operations, as illustrated by the pipettor having moved to a pipette disposal station 150 and has ejected used pipette tips before going back and picking up new ones or to engage/disengage the magnets. Also shown in FIG. 4F is lock 160 for securing the rack to the instrument table. Features such as tongues, grooves, pins, slots are also included 155 to provide better positional accuracy in the automated embodiments. Additional position sensitive devices such as sensors or others may be part of the rack installation and lockdown procedure and these may be electrically readable by the pipettor to ensure positioning accuracy.

Figure 4G:
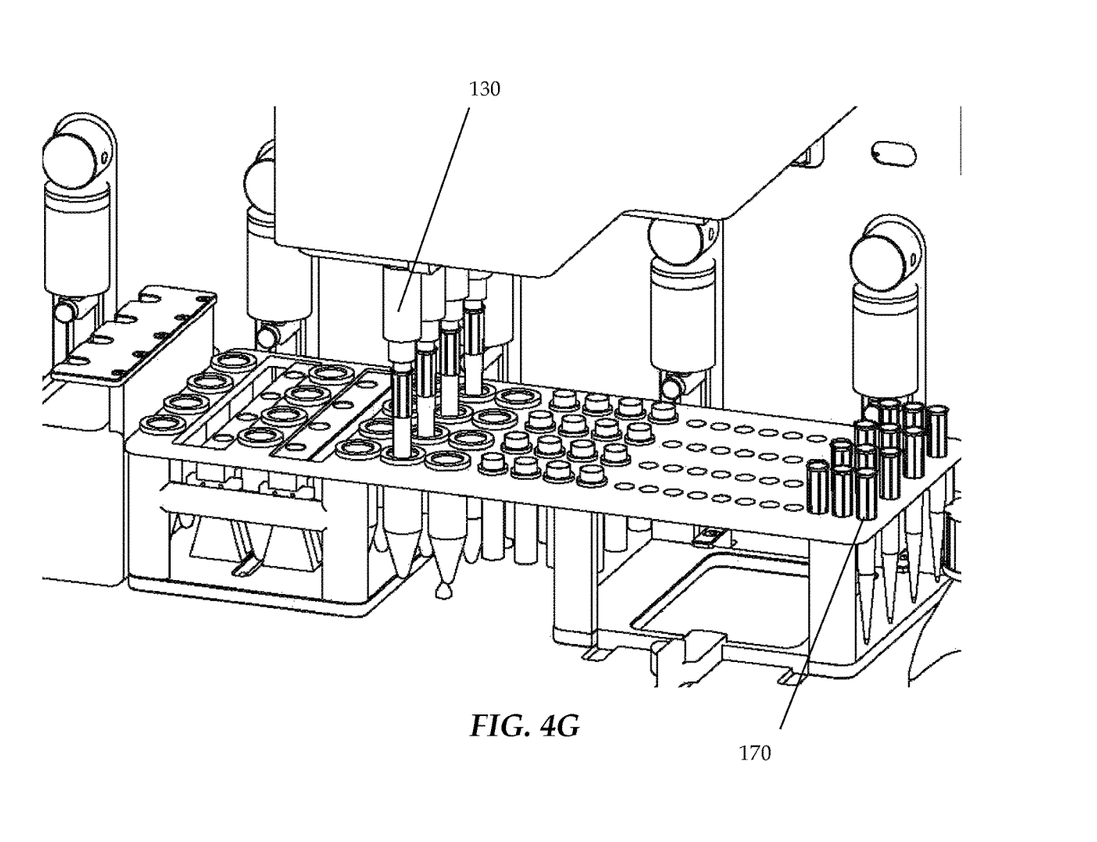
Figure 4H:
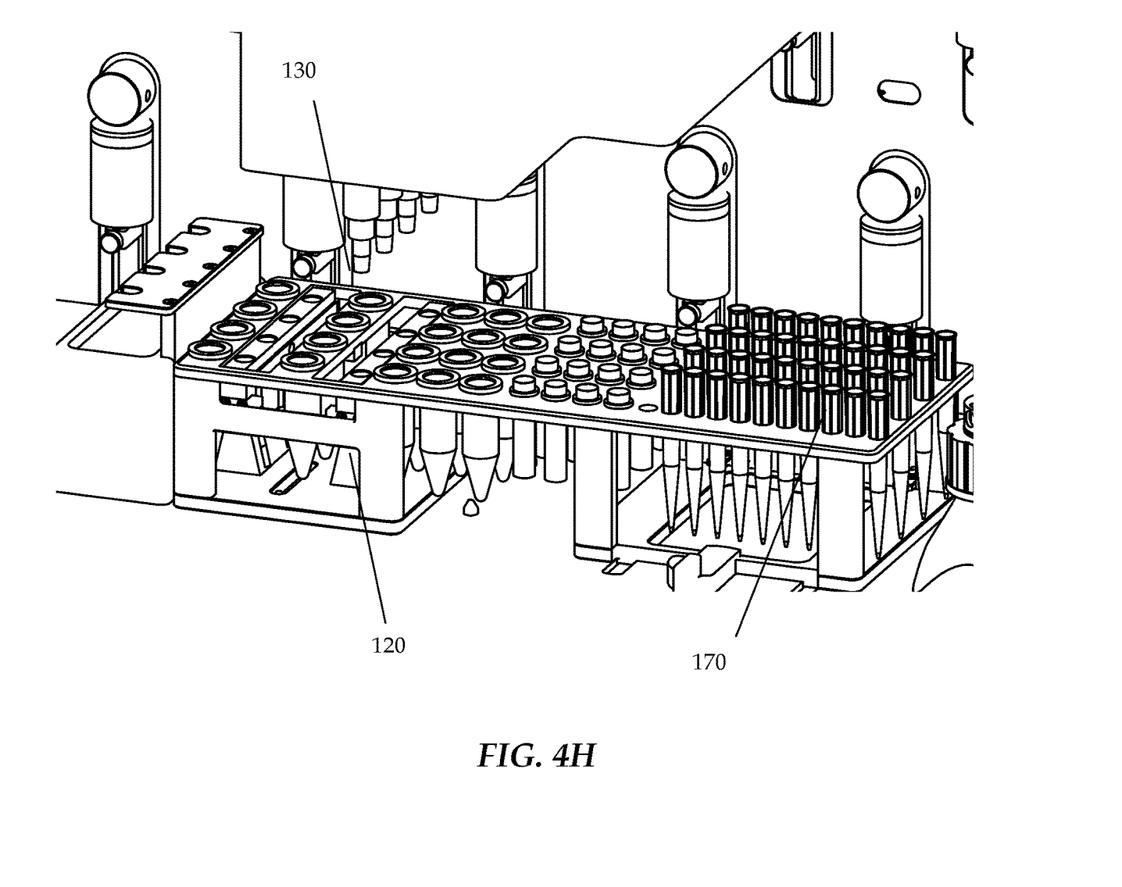
Figure 5A:
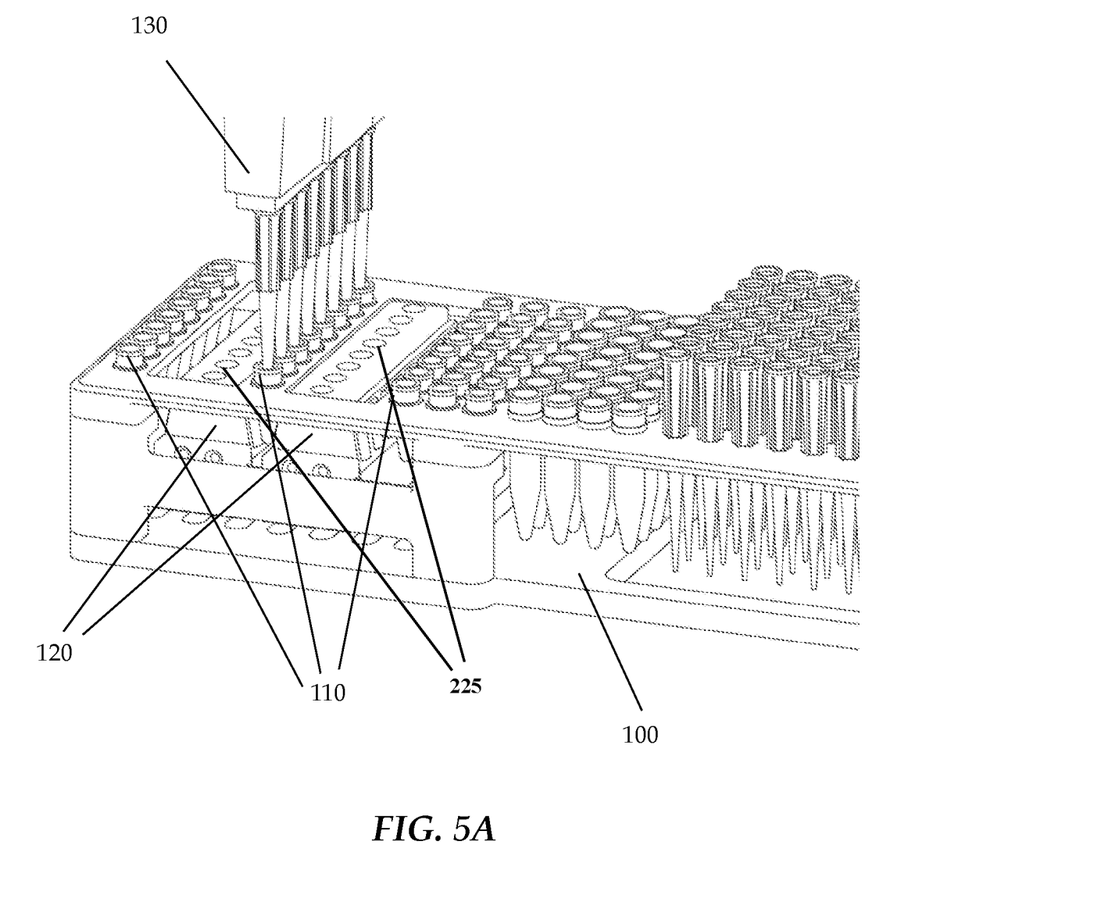
FIGS. 5A, 5B, and 5C show details of exemplary embodiments for a manual liquid handling scenario
Figure 5B:
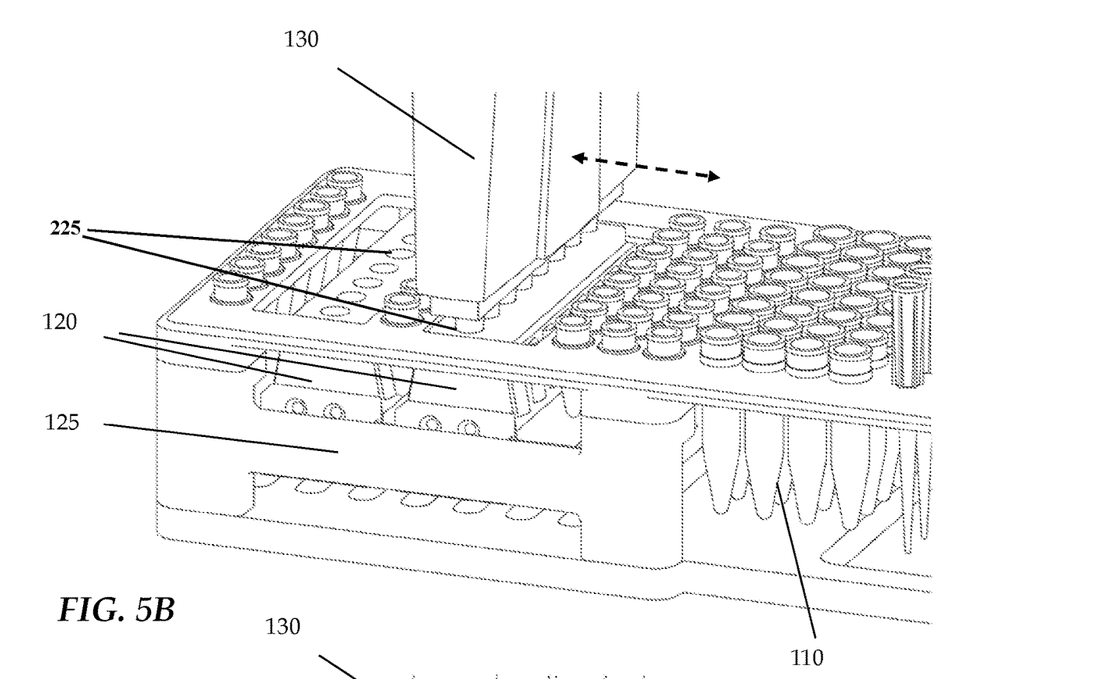
Figure 5C:
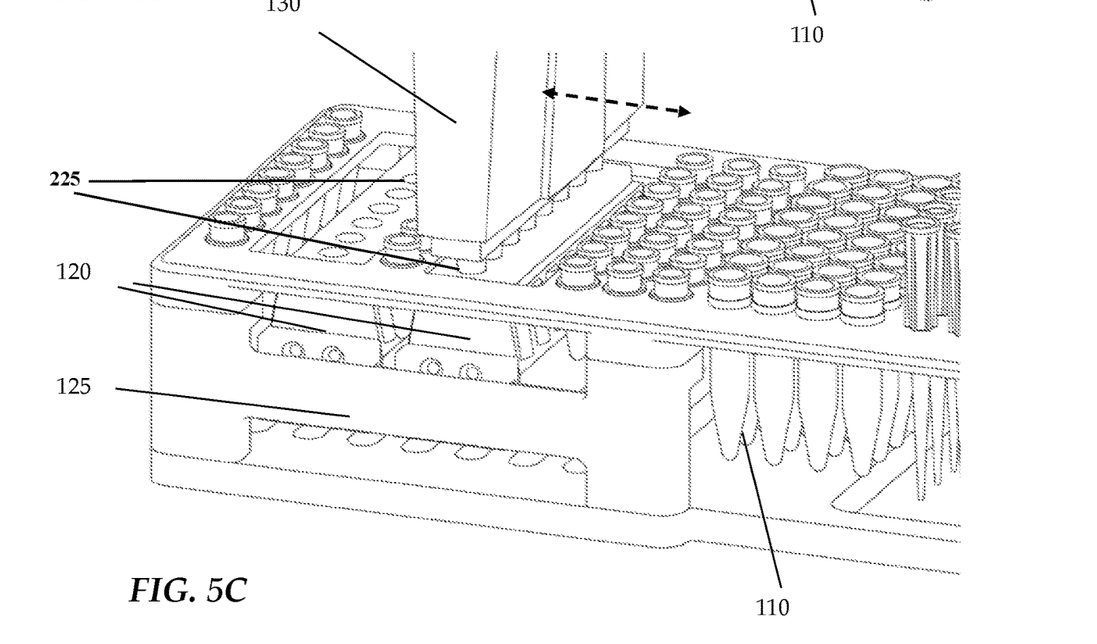

FIG. 4G shows disposable pipettes as they are stored on rack 100. FIG. 4H shows a rack 100 fully loaded with vials 110 and disposable pipettes 170, with pipettor heads 130 ready to move, mate with pipettes and vials an perform desired operations FIGS. 5A, 5B, and 5C show corresponding arrangements for the manual system. Again the magnet/backplate arrangement 120 may be configured with nests 225 for the pipettor head 130, and moved by the pipettor, or other manual actuators may be employed, or even possibly motorized or other electromechanical actuators. As shown in the Figures the magnets have engaged and non-engaged positions, and are positioned in the engaged positions when separation steps are executed.

It should also be noted that wafers of pipettes or vials, which can be prefillable exist and can be configured to snap on and off the rack body. These wafers, essentially a bank of positions can aid in sterile sample handling in a convenient fashion.

Taken together, the suitably configured rack mated to a compatible pipettor and utilizing a magnetic mode for sample separation, an operable system for magnetic-based sample preparation is enabled. The examples shown in the Figures use side engaged magnets with a fixed 4 head/pipette liquid handler, which as described above are particularly suitable for both positive and negative selection mode separations. However, similar selection methods could be accommodated on a different integrated rack, with variations/adaptations in magnetic arrangement. The rack may also be mate-able with another position or mate-able device, of types either currently or potentially available in the future, specifically configured for positive selection, thus creating a single sample preparation station easily switchable between positive and negative mode selection.

By way of illustrating the effectivity of the automated system embodiment used for depletion mode separation, the advantages realized by the practicing depletion mode on this system will now be described.

The example system embodiment shown may be programmed to isolate target moieties from up to 4 samples simultaneously. Serial and/or cocktail formulations of antibodies are possible. Automated depletion saves time, improves efficiency, and minimizes variability between separations. Upon completion of separation cycle, moieties of interest are immediately available for a number of different downstream techniques and applications. For reasons described above, negative selection could provide highly beneficial capabilities that will are difficult to replicate with positive selection.

The negative selection mode/feature provides enrichment technology by way of depletion directly from variety of sample types. This capability supports depletion of non-target moieties, providing a greatly enriched and label-free target populations. With Depletion mode the system performs fast, automated, and column-free elimination of non-targets with minimal sample handling. User loads cell sample and reagents into the instrument to start the isolation. Minimal technical "hands-on" time per run is required. Immuno-magnetic labeling and magnetic separation steps using disposable pipette tips, eliminates cross-contamination and allows safe handling of blood products. The product of this protocol can be further enriched by specific markers or can be used as a direct input through a number of downstream characterization methods. Innovation is in correct formulation of reagents and magnetic bead complexes against cells of non-interest in sequential or combined/cocktailed format from a single sample. The depletion mode functionality described herein can be added to suitable pipettors/liquid handlers with a rack as disclosed herein, and a configuration (programming) of the pipettor.

The manual arrangement may achieve similar beneficial results.

Figure 6:
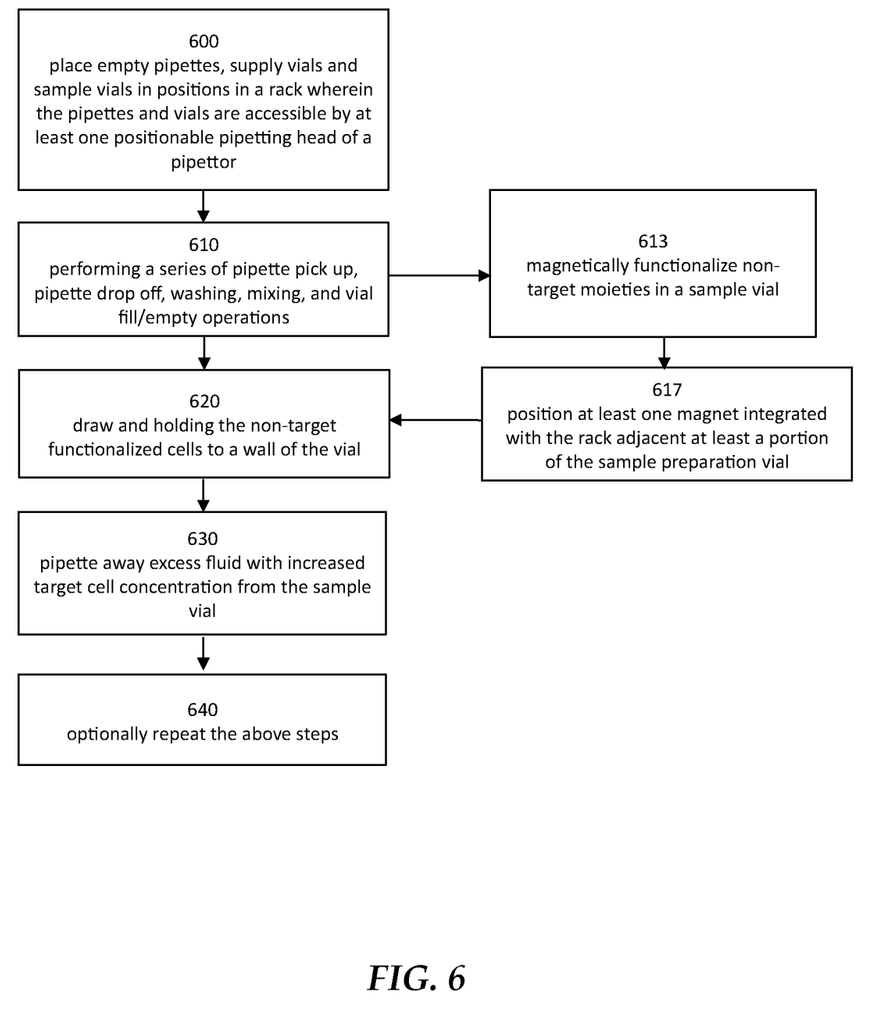
FIG. 6 is a flow chart of a depletion-based method using the rack of the current disclosure

FIG. 6 us a flow chart of an exemplary method for performing a depletion separation process using a rack as disclosed herein along with a suitable liquid handler/pipettor.

In step 600 the rack is loaded by placing supply vials, sample vials, empty pipettes in positions on the rack where the pipettes and vials are accessible by a positionable pipetting head of the pipettor. The pipettor heads may be positionable under automated control or manual control depending on the type of pipettor used. It is understood that the exact mix of vials and pipettes will vary with specific application and all type or a subset of types may be employed.

In step 610. a series of pipette pick-up/drop-off, washing, mixing and vial fill/empty operations are performed. Specific operations for depletion may include such as step 613 magnettically finctionalize non-target moieties in a sample vial, and positioning at least one magnet in step 617 adjacent the vial with the functionalized solution. In some embodiments the functionalized solution is prepared on the rack as part of the pipetting steps.

In step 620 the functionalized non target moieties are drawn to the wall adjacent the positioned magnet. More than one magnet may be used, the idea being to pin the analytes/cells that have been functionally magnetized to the vial.

In step 630 excess fluid is removed. Since the non-target moieties are pinned to the vial, the excess fluid has an increased concentration of target moieties. This target rich solution is used for subsequent analysis, such as liquid biopsy, thus the disclosed method using the novel rack operating in depletion mode is an example of a suitable sample preparation technique for liquid biopsy. Other analysis techniques may benefit from variations of the rack/pipettor system In step 640, any or all of the above steps may be used to further separate the moieties. For instance, the excess fluid may be re-separated to draw out any remaining non-targeted species as many times as desired.

The embodiments described herein are exemplary. Modifications, rearrangements, substitute materials, alternative elements, etc. may be made to these embodiments and still be encompassed within the teachings set forth herein.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y or Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to illustrative embodiments, it will be understood that various omissions, substitutions, and changes in the form and details of the devices and components illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. An automated liquid biopsy sample preparation system comprising:
    a rack, comprising:
        a mounting surface with a plurality of mounting positions defined by holes for vials and pipettes wherein the rack is configured to hold empty pipettes and a combination of a plurality of sample and supply vials at the plurality of mounting positions in the mounting surface, the mounting positions arranged in at least a first row, second row, and third row, and compatible with at least one automated pipettor, wherein the pipettor comprises a plurality of heads;
        at least two slidable magnets, where a first magnet is disposed between the first row and the second row and a second magnet is disposed between the first row and the third row, the first magnet is mounted on a first backplate and second magnet is mounted on a second backplate, each of the first and second backplates comprising holes on a top thereof wherein the pipettor heads drop down and insert into the holes on the top of the first backplate or the second backplate and drive the first backplate or the second backplate to slide to horizontally move the first magnet or the second magnet on the rack;

the at least one automated pipettor compatible with the mounting position spacing on the rack, comprising:
a vertical and horizontal actuator configured to translate at least one pipettor head to mounting positions wherein the pipettor head is configured to at least one of pick up pipettes, drop pipettes, fill vials with fluid from pipettes, and withdraw fluid from vials into pipettes at the mounting positions on the rack; and
at least one pipette configured to fill and empty fluidics in fluid communication with the pipettor head;

wherein when with the rack is loaded with a plurality of pipettes, empty vials and vials with fluids the system is configured to execute a magnetic based sample preparation solely in the rack with a fluid sample containing a population of magnetic beads functionally adhered to non-target moieties of biological cells.

2. The system of claim 1 further comprising at least one pipette disposal position accessible by at least one of the pipettor heads for changing out of pipettes between fill, empty, washing, mixing, and magnet movement operations.

3. The system of claim 1 wherein supply vial mounting positions may accept sample of interest vials, washing solution vials, reagent vials, and magnetic bead suspension vials.

4. The system of claim 1 wherein the mounting positions are arranged wherein multiple positions are in parallel with spacing compatible with a corresponding number of parallel pipettor heads configured to allow parallel operation on multiple vials and pipettes.

5. The system of claim 4 comprising at least one additional slidable, magnet or set of magnets is disposed to at least one of be positionable to a side of the parallel sample preparation vials or positionable to a second set of parallel vials.

6. The system of claim 4 wherein vial mounting positions are linearly arranged in parallel rows with the spacing between the rows set by the separation of the parallel pipettor heads.

7. The system of claim 1 wherein the first and second magnets are configured to match a shape of at least one type of vial.

8. The system of claim 1 wherein the first and second magnets and backplates are slidable on rails.

9. The system of claim 1 wherein the rack is configured to be locked in place under the pipettor to a support surface to maintain positional accuracy for subsequent operations.

10. The system of claim 1 wherein the first and second magnets are configured for negative selection sample preparation.

11. A magnetic process for preparing magnetically separated samples, using the automated liquid biopsy sample preparation system of claim 1, comprising:
placing empty pipettes, a plurality of supply vials and sample vials in positions in a rack wherein the pipettes and vials are accessible by a pipettor comprising a plurality of heads;
performing a series of pipette pick up, pipette drop off, washing, mixing, and vial fill/empty operations comprising:
magnetically functionalizing non-target moieties of cells in at least one sample preparation vial;
positioning at least two magnets each mounted on a backplate, each backplate with holes-on a top thereof, each backplate integrated with the rack;
positioning a first magnet between the first row and the second row;
positioning a second magnet between the first row and the third row; and
wherein the plurality of pipettor heads, that drop down from above into the holes on top of one of the backplates and drive either the first backplate or the second backplate to slide horizontally to move the first magnet or the second magnet on the rack.

12. The process of claim 11 wherein the magnetic sample process is a negative selection process, further comprising drawing and holding the magnetically functionalized non-target moieties to a wall of the vial; pipetting away excess fluid with increased target cell concentration from the sample vial.

13. The process of claim 11 wherein vial mounting positions and pipette mounting positions each comprises multiple positions in parallel accessible by multiple parallel pipettor heads.

14. The process of claim 11 wherein the supply vial mounting positions accept sample of interest vials, washing solution vials, buffer solution vials, reagent vials and/or magnetic bead suspension vials.

15. The process of claim 11 further comprising producing functionalized sample solution by mixing the sample with a magnetic bead solution and optionally buffer solutions on the rack using the pipettor.

16. The process of claim 11 further comprising disposing of pipette heads at a pipette disposal position in between operations.

17. The process of claim 11 wherein target cells are cancer cells.

* * * * *